(12) United States Patent
Mason et al.

(10) Patent No.: US 11,964,796 B2
(45) Date of Patent: Apr. 23, 2024

(54) STRUCTURE FOR THE PACKAGING OF PRIMARY CONTAINERS FOR PHARMACEUTICAL USE

(71) Applicant: NUOVA OMPI S.R.L., Padua (IT)

(72) Inventors: Diego Mason, Padua (IT); Gianpaolo Bertolin, Padua (IT)

(73) Assignee: Nuova Ompi S.r.l., Piombino Dese (IT)

( * ) Notice: Subject to any disclaimer, the term of this patent is extended or adjusted under 35 U.S.C. 154(b) by 59 days.

(21) Appl. No.: 17/627,199

(22) PCT Filed: Jun. 25, 2020

(86) PCT No.: PCT/IB2020/056005
§ 371 (c)(1),
(2) Date: Jan. 14, 2022

(87) PCT Pub. No.: WO2021/009585
PCT Pub. Date: Jan. 21, 2021

(65) Prior Publication Data
US 2022/0258921 A1   Aug. 18, 2022
US 2024/0067403 A2   Feb. 29, 2024

(30) Foreign Application Priority Data
Jul. 17, 2019   (IT) .................. 102019000011982

(51) Int. Cl.
*A61J 1/14*    (2023.01)
*B65D 25/10*   (2006.01)
*A61M 5/00*    (2006.01)

(52) U.S. Cl.
CPC ............... *B65D 25/108* (2013.01); *A61J 1/14* (2013.01); *A61M 5/002* (2013.01)

(58) Field of Classification Search
CPC ... A61M 5/002; A61J 1/14; A61J 1/16; B65D 25/108; B65D 25/10; B65D 77/2024
(Continued)

(56) References Cited

U.S. PATENT DOCUMENTS 9,718,583 B2 *  8/2017  Nicoletti ................ B65D 65/02
9,919,094 B2 *  3/2018  Shimazaki ............. A61M 5/284
(Continued)

FOREIGN PATENT DOCUMENTS

EP   2865400 A1   4/2015
EP   3269409 A1   1/2018
(Continued)

OTHER PUBLICATIONS

Partial English translation of Italian Search Report for IT Patent Application No. 20190001982, mailed Mar. 11, 2020, 9 pages.
(Continued)

*Primary Examiner* — Steven A. Reynolds
(74) *Attorney, Agent, or Firm* — Armstrong Teasdale LLP

(57) ABSTRACT

A structure (4) for the packaging of containers for pharmaceutical use (8) comprising: a support plane (20) fitted with a plurality of seats (24,48) for housing containers for pharmaceutical use (8), the seats (24,48) having main extension axes (X-X), parallel to each other, the seats (24,48) being delimited by side walls (32) extending from a lower end (36) to an upper end (40), said upper end (40) facing and being configured to receive in abutment a collar (44) of an associable container (8) for pharmaceutical use. The perimeter seats (48), arranged externally along a perimeter edge (52) of the support plane (20), have, at the lower end (36), at least one guide or chamfer (56) diverging as it moves away from the lower end (36), opposite the upper end (40).

17 Claims, 5 Drawing Sheets

(58) Field of Classification Search
USPC .................................... 206/438, 364, 571
See application file for complete search history.

(56) References Cited

U.S. PATENT DOCUMENTS

| | | | | |
|---|---|---|---|---|
| 10,227,161 B2* | 3/2019 | Auerbach | ............. | A61M 5/008 |
| 11,161,671 B2* | 11/2021 | Yoshida | ................ | A61M 5/008 |
| 11,419,975 B2* | 8/2022 | Mason | ................. | B65D 25/108 |
| 2012/0181285 A1* | 7/2012 | Krauss | ..................... | A61J 1/16 |
| | | | | 220/507 |
| 2013/0048531 A1* | 2/2013 | Nicoletti | ............... | A61M 5/008 |
| | | | | 206/557 |
| 2013/0186793 A1* | 7/2013 | Gagnieux | ............. | A61M 5/002 |
| | | | | 206/364 |
| 2014/0027332 A1* | 1/2014 | Pawlowski | ............... | A61J 1/14 |
| | | | | 248/346.03 |
| 2015/0108020 A1* | 4/2015 | Iwase | .................... | A61M 5/008 |
| | | | | 206/365 |
| 2015/0190566 A1* | 7/2015 | Okihara | .............. | A61M 5/3134 |
| | | | | 206/365 |
| 2019/0343721 A1* | 11/2019 | Komann | ................ | B65D 71/70 |
| 2020/0114063 A1* | 4/2020 | Vivien | .................. | A61M 5/008 |
| 2020/0156824 A1* | 5/2020 | Komann | ............... | A61M 5/008 |

FOREIGN PATENT DOCUMENTS

| | | |
|---|---|---|
| WO | 2011110872 A1 | 9/2011 |
| WO | 2018198028 A1 | 11/2018 |

OTHER PUBLICATIONS

International Search Report and Written Opinion for International Patent Application No. PCT/IB2020/056005, mailed Oct. 6, 2020, 10 pages.

* cited by examiner

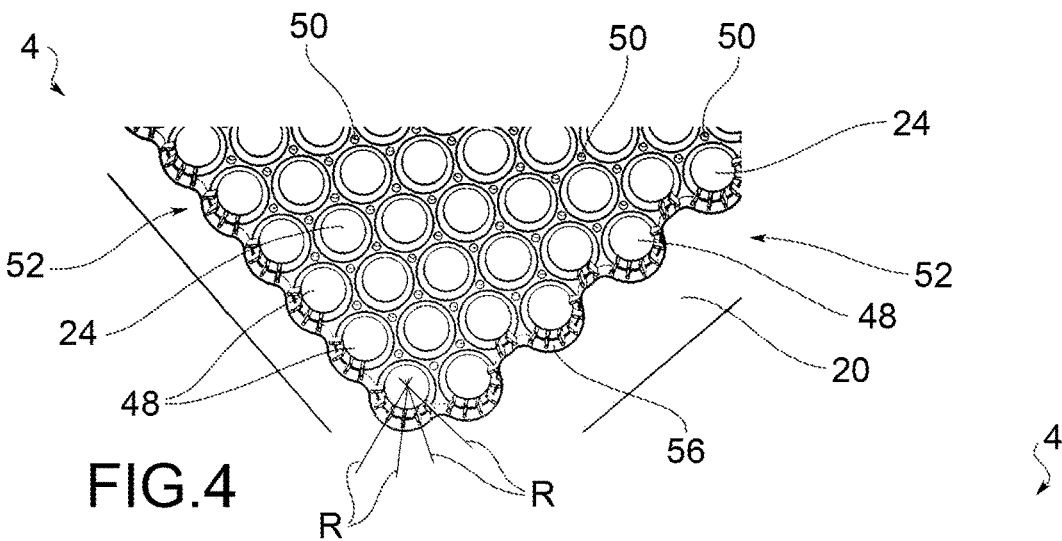
FIG.4
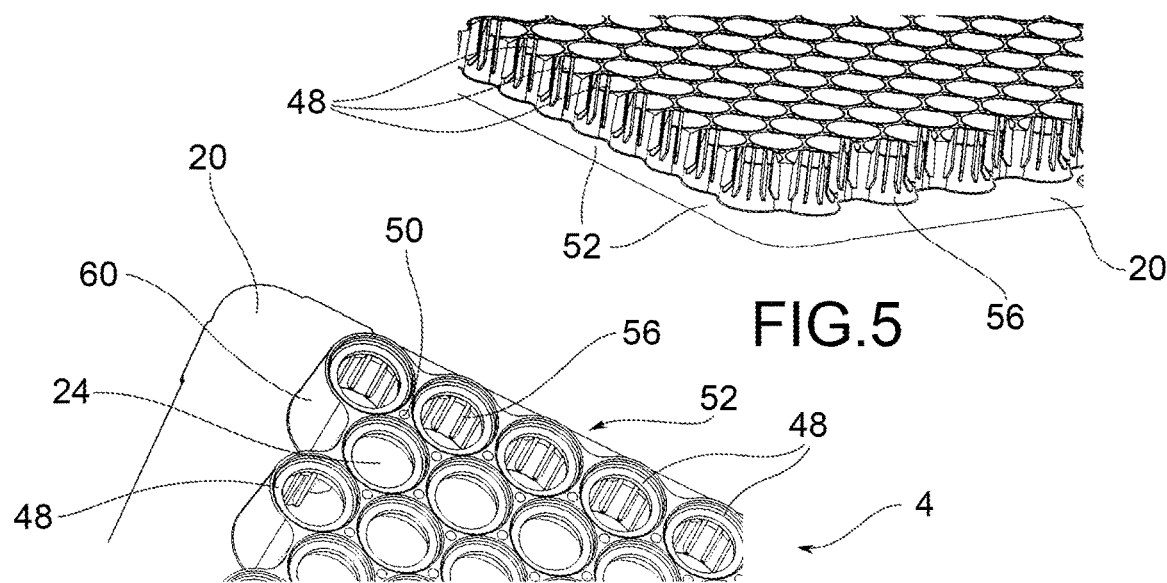
FIG.5
FIG.6
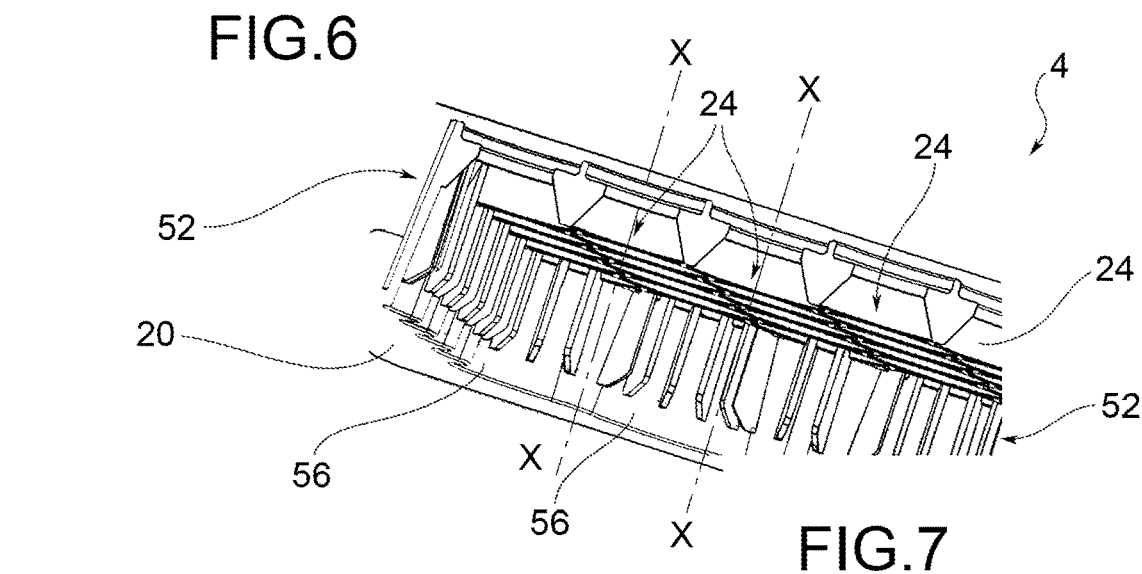
FIG.7

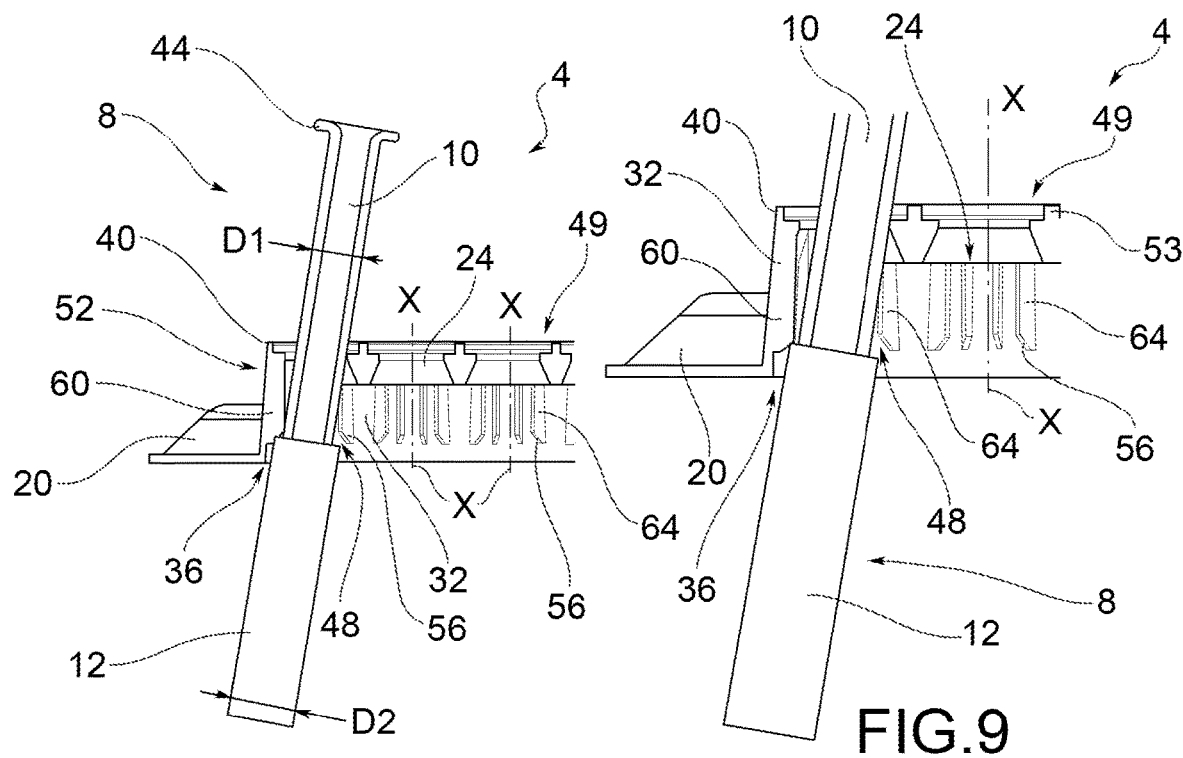

STRUCTURE FOR THE PACKAGING OF PRIMARY CONTAINERS FOR PHARMACEUTICAL USE

CROSS-REFERENCE TO RELATED APPLICATIONS

This application is a U.S. National Phase filing of PCT International Patent Application No. PCT/IB2020/056005, having an international filing date of Jun. 25, 2020, which claims priority to Italian Patent Application No. 102019000011982, filed Jul. 17, 2019, each of which is hereby incorporated by reference in its entirety.

FIELD OF APPLICATION

The present invention relates to a structure for the packaging of pharmaceutical containers.

BACKGROUND ART

It is known that primary containers for pharmaceutical use, such as vials, bottles, tubular injection vials, and syringes must be kept in a controlled, clean, and sterile environment isolated from the outside until they are used or employed in treatment processes, in particular filling and closing.

Structures for the packaging of containers for pharmaceutical use are known comprising a tray, referred to as a "tub", made of plastic material and with a closed bottom, which supports a support plane or matrix therein (referred to as a "nest"), typically made of plastic material, and having several housing holes in which the primary containers for pharmaceutical use are housed with vertical orientation.

Some types of containers for pharmaceutical use, such as syringes, can be held in place by resting the perimeter collar on the edge of the housing holes, while other containers, free from protruding parts, need specific elements to retain them inside the holes.

In turn, such packaging structures (referred to as tubs and nests), appropriately sealed, are placed inside containers having a suitable size and weight to be handled during the packaging and unpacking operations.

Therefore, such packaging structures (tubs and nests) are also repeatedly handled by automatic mechanical arms to be transported, repositioned, tipped, and stored.

For this purpose, the need is felt to create packaging structures which are as light as possible and which, at the same time, ensure a suitable mechanical rigidity.

Indeed, the support planes (nests), in particular, tend to inflect downwards under their own weight and also, above all, under the weight of the dozens of primary containers that they must house and support. Such a weight is further increased when said primary containers are filled with medical substance. Such an inflection must be as limited as possible because the containers lose their reciprocal parallelism with respect to a vertical direction, perpendicular to the support plane.

As a result, the containers would tend to collide with one another, and inflection would complicate both the operation of inserting and extracting the containers into and from the nest and the operation of filling them at the end user.

This inflection must be avoided or, in any case, controlled with high precision because the packaging structures must be moved automatically by means of mechanical arms which could interfere with some of said containers, if they are badly positioned/orientated inside the respective seats of the support plane, in particular with the steps of introducing and extracting the primary containers from the nest.

Therefore, an excessive nest inflection increases the risk of collisions between the grippers and containers and limits the automation possibilities for gripping and handling the containment structures.

Furthermore, the deformation of the nests facilitates the mutual contact between containers which could chip as a result of impacts, both at the projecting bodies and at the respective collars.

Shocks must be prevented because they could generate cracks, even micro-cracks, with the consequent risk of subsequent breakage of the containers.

Such shocks must be avoided not only at the tubular bodies of the containers but also at the respective gripping collars.

Obviously, the need to reduce the weight of the nest contrasts with respect to the need to reduce the stiffness of the containment structures. Indeed, weight reduction is normally achieved by eliminating material, thinning thicknesses, creating notches, and lightening holes. These expedients inevitably weaken the mechanical rigidity of the structure, which tends to deform excessively.

There is also an additional technical problem in which the primary containers have a double diameter, in particular, a smaller portion with a larger diameter and a larger portion with a smaller diameter. It is worth noting that the concept of lower and upper portion is linked to the positioning of the primary containers on the nest; in other words, the upper portion comprises the collar which abuts on the respective seat obtained on the nest; therefore, the upper portion is the that embodying the support of the primary container. The lower portion, with a larger diameter, is the portion that is always projecting, while the upper portion is the one that is gripped by the automatic grippers (or similar automatic gripping and handling devices) to extract the container from its seat.

Since the lower portion is the portion with the largest diameter, a stepped or undercut portion is made in the lifting movement of the primary container from the respective seat at the transition from the smaller diameter to the larger diameter with respect to the extraction or lifting movement of the container from the bottom to the top.

If the lifting of the container is not perfectly perpendicular to the nest support plane (i.e. to the ground), such an undercut portion easily tends to stick to the lower portion of the container housing. Such a sticking must be absolutely avoided because, on the one hand, it blocks the extraction automatism (or at least partial lifting) of the containers and, on the other hand, it causes collisions between adjacent containers with the possible risk of damage/chipping thereof.

PRESENTATION OF THE INVENTION

Therefore, the need is felt to solve the drawbacks and limitations mentioned above with reference to the prior art.

Therefore, the need is felt to provide a structure for the packaging of containers for pharmaceutical use that is at the same time light and resistant to allow a correct grip and handling of the structure itself in a fast and automated manner, without running the risk of sticking and/or accidental contact between the gripping devices and the containers or between adjacent containers resulting from their misalignment with respect to a vertical direction.

Such a need is met by a structure for the packaging of pharmaceutical containers according to claim 1.

DESCRIPTION OF THE DRAWINGS

Further features and advantages of the present invention will become more comprehensible from the following description of preferred embodiments given by way of non-limiting examples, in which:

FIGS. 4-7 are perspective section views, from various angles, of enlarged details of the containing structure in FIG. 1;

FIG. 8 is a section view of a containment structure according to the present invention with a container housed in a perimeter seat;

FIG. 9 is an exploded view of FIG. 9;

FIG. 10 is a section view of a containment structure according to the present invention with a container housed in an inner seat;

FIG. 11 is an exploded view of FIG. 10;

Elements or parts in common to the embodiments described will be indicated hereafter using the same reference numerals.

DETAILED DESCRIPTION

Figure 1:
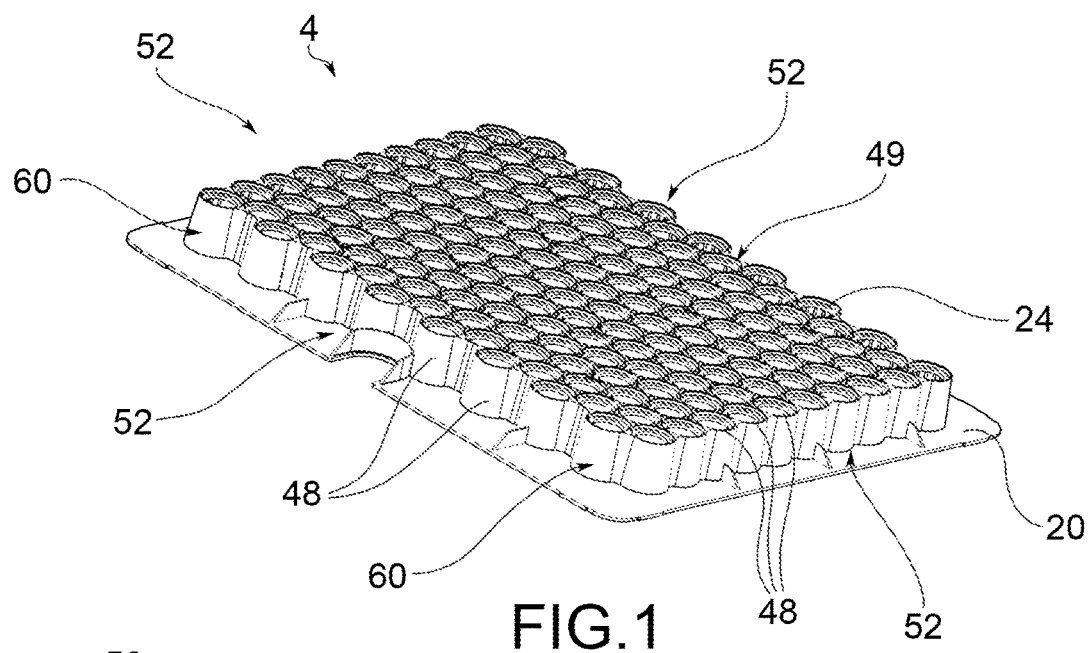
FIG. 1 is a top perspective view of a structure for the packaging of containers for pharmaceutical use, according to the present invention.
Figure 2:
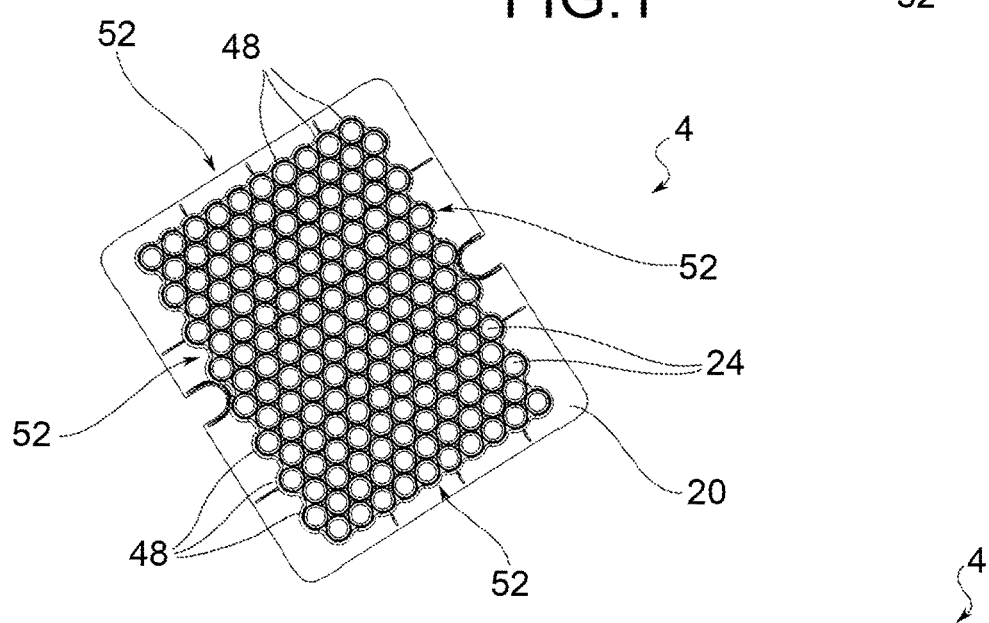
FIG. 2 is a top plan view of the containing structure in FIG. 1.
Figure 3:
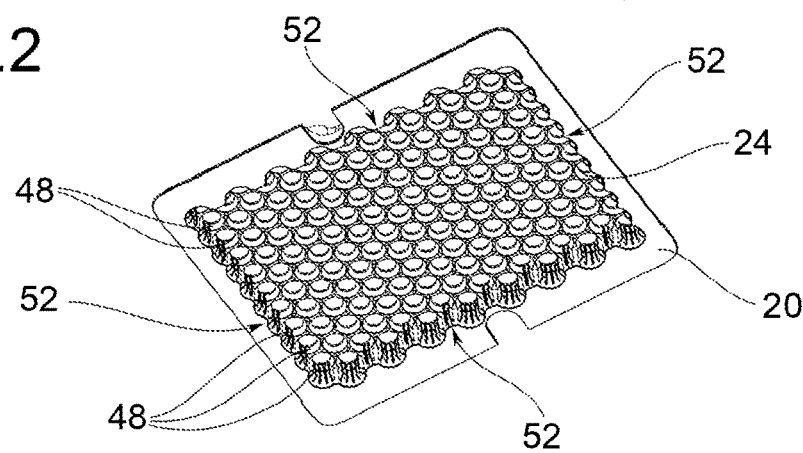
FIG. 3 is a bottom perspective view of the containing structure in FIG. 1.
Figure 12:
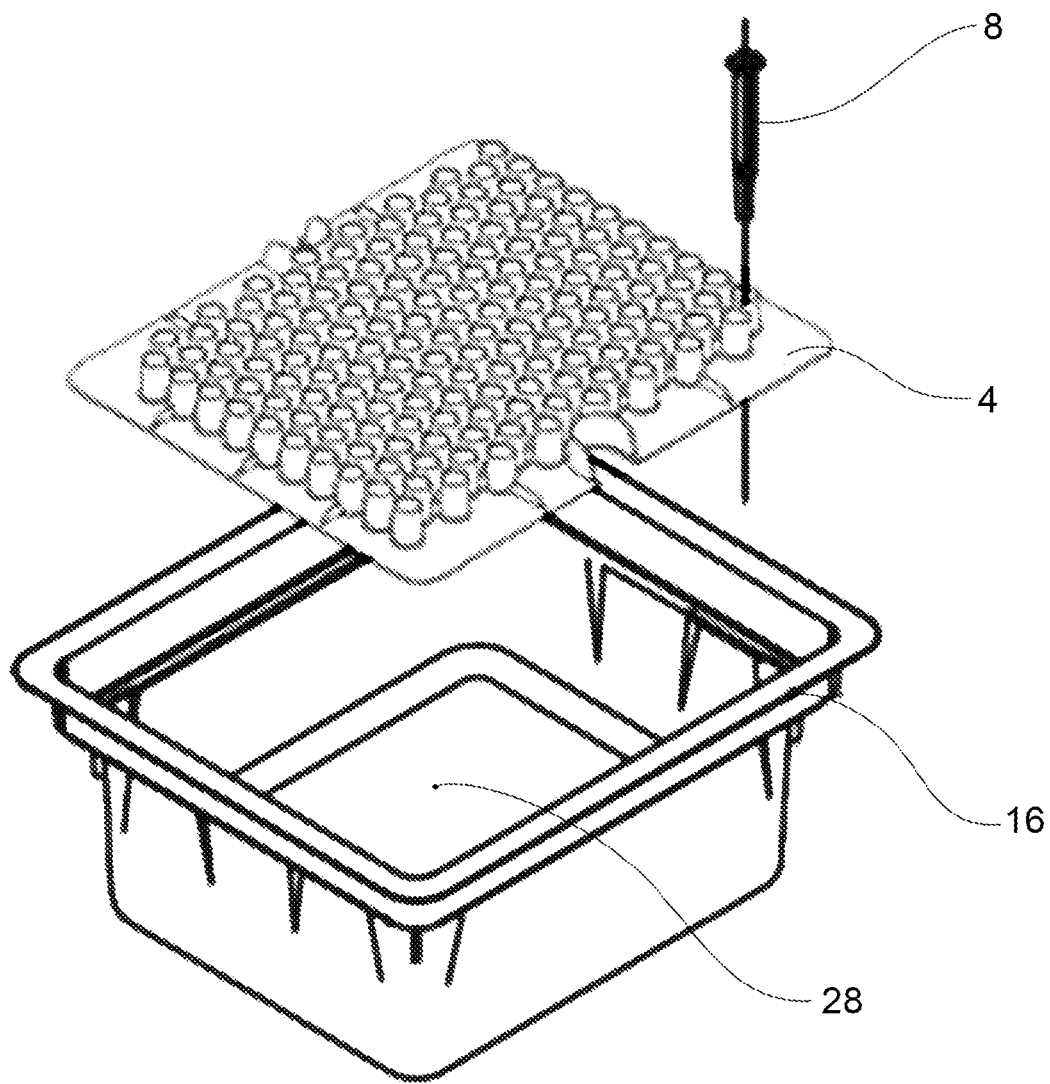
FIG. 12 is a perspective section view of the tray (tub)/containment structure (nest) assembly, according to an embodiment of the present invention.
Figure 13:
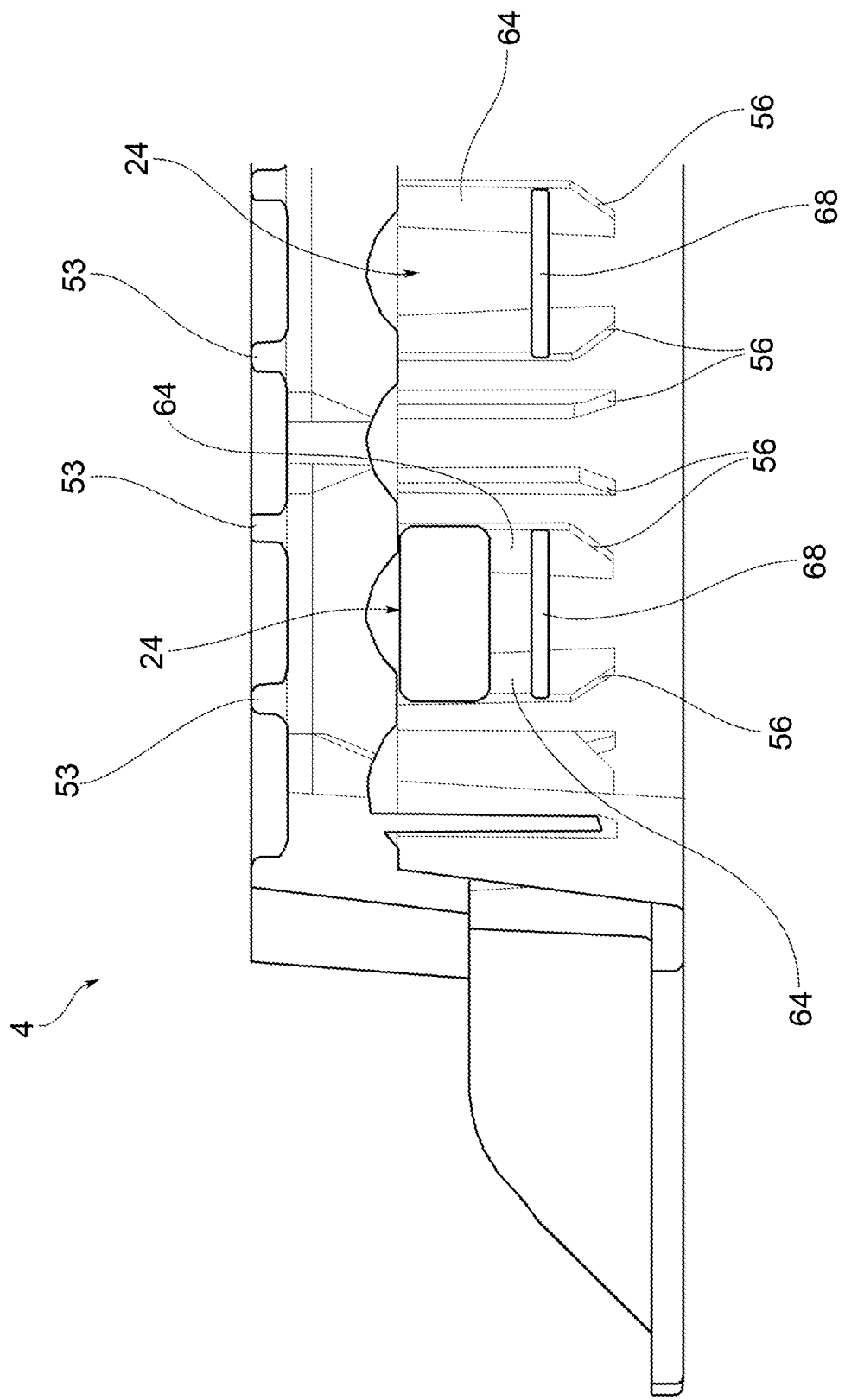
FIG. 13 is a perspective section view of a containing structure, according to a further embodiment of the present invention.

With reference to the aforementioned figures, reference numeral 4 indicates an overall view of a structure for packaging containers 8 for pharmaceutical use.

It is worth noting that, for the purposes the scope of protection of the present invention, the specific type of containers for pharmaceutical use is not relevant, meaning containers of various types, sizes and/or materials, such as syringes, vials, tubular injection vials, bottles and the like or medical devices with or without means of containing a pharmaceutical, such as autoinjectors with or without Carpule or the like.

In particular, as shown in greater detail below, the present invention is advantageously applied when containers 8 having a double diameter, i.e. a first portion or upper portion 10 having a first diameter D1 and a second portion or lower portion 12 having a second diameter D2, preferably larger than said diameter D1, are used.

The structure 4 comprises a tray 16 which houses and supports a support plane 20 provided with a plurality of seats 24 for housing said containers 8 for pharmaceutical use.

Furthermore, the tray 16 has a bottom 28, which is preferably closed.

The seats 24 have main extension axes X-X, parallel to each other.

Typically, the seats 24 have a cylindrical shape with respect to main extension axes X-X, parallel to one another. Such main extension axes are preferably perpendicular to the support plane 20.

The seats 24 being delimited by side walls 32 which extend from a lower end 36 to an upper end 40, wherein said upper end 40 is facing and configured to receive in abutment a collar or neck 44 of an associable container 8 for pharmaceutical use.

The side walls 32 of the seats 24,48 have cylindrical circular cross-section with respect to a section plane perpendicular to said main extension axes X-X.

Furthermore, the side walls 32 of mutually adjacent seats 24,48 are mutually tangent, thus identifying a plurality of through holes 50.

According to an embodiment, on the side of an upper face 49 of the seats 24,48, intended to receive in abutment the collar 44 of said containers 8 for pharmaceutical use, there is a raised perimeter 53 of each seat 24,48 adapted to delimit and surround at least partially an annular pocket, enlarged with respect to the seat 24,48 and destined to receive in abutment said collar 44.

Advantageously, the perimeter seats 48, arranged externally along a perimeter edge 52 of the support plane 20, have, at said lower end 36, at least one guide or chamfer 56 diverging as it moves away from the lower end 36, opposite to the upper end 40.

According to an embodiment, the side walls 32 of said perimeter seats 48 have a stepped portion 60, connecting to said support plane 20, to create a spacer between the support plane 20 and the upper end 40 of the side walls themselves; preferably, said guide or chamfer 56 is arranged at said stepped portion 60.

The spacer has the further function of stiffening the structure 4 so that it does not inflect under its own weight and the weight of the containers 8 housed in the respective seats 24.

The guide or chamfer 56 is at least partially counter-shaped with respect to the side wall from which it protrudes to direct the container symmetrically towards the centre of the corresponding perimeter seat 48, during both the step of inserting and during the step of extracting.

The guide or chamfer 56 can be made in various geometries or shapes.

According to a possible embodiment, said chamfer 56 is made by means of a continuous shelf projecting from the side wall 32, preferably with respect to each corresponding stepped portion 60.

According to a further embodiment, said chamfer 56 is made by means of a plurality of fins 64, separated or spaced from each other.

Preferably, said fins 64 are arranged in radial R-R directions with respect to the corresponding perimeter seats 48.

According to an embodiment, the side walls 32 of adjacent perimeter seats 48 are at least partially interlocking with one another; this further increases the structural rigidity of the containment structure 4. For example, such an interlocking and/or connection may be achieved by means of brackets or connection rods 68.

According to a possible embodiment, said guide or chamfer 56 has a truncated conical section, with respect to a section plane perpendicular to the support plane 12.

For example, the truncated conical section has a taper angle, with respect to a perpendicular to support plane 12, between 30 and 60 degrees.

Said taper angle can be between 40 and 50 degrees and is preferably 45 degrees.

According to a possible embodiment, said guide or chamfer 56 has a parabolic arc cross-section, with respect to a section plane perpendicular to the support plane 12.

In turn, the side walls 32 of the seats 24,48 have a converging taper from the lower end 36 towards the upper end 40.

Preferably, said taper is either greater than or equal to the taper of said guide or chamfer 56.

The best guide of the containers 8 for pharmaceutical use during the entire step of extracting from the perimeter seats 48 is achieved in this manner.

According to a possible embodiment, said guide or chamfer 56 is aligned with a through opening of the corresponding perimeter seats 48, at the upper end 40, with respect to a vertical direction, perpendicular to said support plane 20 and parallel to said main extension axes X-X.

As can be appreciated from the description above, the present invention allows to overcome the drawbacks presented in the prior art.

First, by virtue of the presence of the perimeter chamfers, there is no risk of sticking during the moving/lifting of the primary containers: indeed, the chamfers accompany the "sliding" of the undercut at the lower wall of the nest ensuring the correct passage of the undercut.

This condition is illustrated in FIGS. 8-11 in which it is shown how the chamfers tend to align the containers without the respective portions passing from the lower portion, with a larger diameter, to the upper portion, with a smaller diameter, being stuck or sticking at the lower portions of the perimeter seats during the step of lifting the containers themselves.

Furthermore, the chamfers create a real guide which ensures a given perpendicularity of the containers with respect to the nest; the risk of accidental contact between adjacent primary containers is avoided in this manner.

Furthermore, the structure has sufficient mechanical stiffness and/or geometric conformation to ensure a reduced elastic deflection of the structure under its own weight and that of the containers it supports, with particular reference to the condition in which the latter are filled.

In this manner, it is always ensured that the containers are correctly aligned within their respective seats, even under conditions of maximum loading of the structure and its containers, e.g. in the case of containers filled with the medicine.

Furthermore, any risk of contact between the collars of nearby containers is prevented, because the collars are contained in pockets or seats delimited by the raised perimeter.

Therefore, said raised perimeters, e.g. in the form of pins or protuberances, prevent any kind of contact between the collars of neighbouring containers.

The parallelism between the containers, with respect to a vertical direction, is ensured not only by the high structural rigidity of the containment structure but also by the fact that the collars rest in abutment on a flat edge with a circular crown shape, being said edge perpendicular to said vertical direction.

Furthermore, the presence of the raised perimeter also ensures the correct radial distance between the containers and, therefore, allow the grippers of a manipulator to be inserted without impact into the gaps between adjacent containers. Such a correct radial distance further helps to avoid the risk of accidental collisions between neighbouring containers.

In order to meet contingent, specific needs, those skilled in the art can make several changes and variations to the structures described above, all contained within the scope of the invention as defined by the following claims.

What is claimed is:

1. A structure for the packaging of containers for pharmaceutical use comprising:
    a support plane fitted with a plurality of seats for housing containers for pharmaceutical use, the seats having main extension axes, parallel to each other,
    the seats being delimited by side walls extending from a lower end to an upper end, said upper end facing and being configured to receive in abutment a collar of an associated container for pharmaceutical use,
    wherein perimeter seats, arranged externally along a perimeter edge of the support plane, each have, at said lower end, at least one guide or chamfer diverging as it moves away from the lower end, opposite the upper end,
    wherein each said guide or chamfer respectively includes a plurality of internal fins separated or spaced from each other along an internal surface of the respective side wall of the perimeter seat, and
    wherein on the side of an upper face of the seats, there is a raised perimeter of each seat that delimits and surrounds at least partially an annular pocket, enlarged with respect to the seat and configured to receive in abutment the collar of the associated container.

2. The structure for the packaging of containers for pharmaceutical use according to claim 1, wherein the side walls of said perimeter seats have a stepped portion, connecting to said support plane, so as to create a spacer between the support plane and the upper end, and wherein said guide or chamfer is arranged at said stepped portion.

3. The structure for the packaging of containers for pharmaceutical use according to claim 1, wherein said guide or chamfer is made by means of a continuous shelf projecting from the side wall.

4. The structure for the packaging of containers for pharmaceutical use according to claim 2, wherein said guide or chamfer is made by means of a continuous shelf projecting from each corresponding stepped portion.

5. The structure for the packaging of containers for pharmaceutical use according to claim 1, wherein the guide or chamfer is at least partially counter-shaped with respect to the side wall from which it abuts so as to direct the container for pharmaceutical use symmetrically towards a center of the corresponding perimeter seat.

6. The structure for the packaging of containers for pharmaceutical use according to claim 1, wherein said fins are arranged in radial directions with respect to the corresponding perimeter seats.

7. The structure for the packaging of containers for pharmaceutical use according to claim 1, wherein the side walls of neighboring perimeter seats are at least partially interlocking or connected.

8. The structure for the packaging of containers for pharmaceutical use according to claim 1, wherein said guide or chamfer has a truncated conical section, with respect to a cross-section plane perpendicular to the support plane.

9. The structure for the packaging of containers for pharmaceutical use according to claim 8, wherein said truncated conical section has a taper angle, with respect to a perpendicular to the support plane, between 30 and 60 degrees.

10. The structure for the packaging of containers for pharmaceutical use according to claim 9, wherein said taper angle is between 40 and 50 degrees.

11. The structure for the packaging of containers for pharmaceutical use according to claim 1, wherein said guide or chamfer has a parabolic arc cross-section with respect to a cross-section plane perpendicular to the support plane.

12. The structure for the packaging of containers for pharmaceutical use according to claim 1, wherein the side walls of the seats have a taper converging from the lower end towards the upper end.

13. The structure for the packaging of containers for pharmaceutical use according to claim 12, wherein said taper is greater or equal to the taper of said guide or chamfer.

14. The structure for the packaging of containers for pharmaceutical use according to claim 1, wherein the side walls of the seats are cylindrical with a circular cross-section with respect to a cross-section plane perpendicular to said main extension axes.

15. The structure for the packaging of containers for pharmaceutical use according to claim 1, wherein the side walls of adjacent seats are tangent to each other, identifying a plurality of through holes.

16. The structure for the packaging of containers for pharmaceutical use according to claim 1, wherein said guide or chamfer is aligned with a through opening of the corresponding perimeter seats, at the upper end, with respect to a vertical direction, perpendicular to said support plane.

17. The structure for the packaging of containers for pharmaceutical use according to claim 10, wherein said taper angle is equal to 45 degrees.

* * * * *